US00PP31841P2

(12) United States Plant Patent

Klemm et al.

(10) Patent No.: US PP31,841 P2
(45) Date of Patent: Jun. 2, 2020

(54) *PETUNIA* PLANT NAMED 'KLEPH18130'

(50) Latin Name: *Petunia hybrida*
Varietal Denomination: KLEPH18130

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,867

(22) Filed: Jun. 20, 2019

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.1, 356.13
See application file for complete search history.

*Primary Examiner* — Susan McCormick Ewoldt
(74) *Attorney, Agent, or Firm* — Cochran Freund & Young LLC; James Weatherly

(57) ABSTRACT

A new *Petunia* plant particularly distinguished by black-purple flowers with a yellow border and a semi-trailing habit, is disclosed.

1 Drawing Sheet

Genus and species: *Petunia hybrida.*
Variety denomination: 'KLEPH18130'.

BACKGROUND OF THE NEW PLANT

The present invention comprises a new and distinct variety of *Petunia*, botanically known as *Petunia hybrida*, and hereinafter referred to by the variety name 'KLEPH18130'. 'KLEPH18130' originated from a cross-pollination conducted in July 2014 in Latina, Italy between the proprietary female *Petunia* variety 'PH-2014-0317' (unpatented) and the proprietary male *Petunia* variety 'PH-2014-0319' (unpatented).

The seeds from the cross were sown and plants were grown in a greenhouse for evaluation, where an individual plant designated 'KLEPH18130' was selected from the group of plants in April 2015 in Latina, Italy. In May 2015, 'KLEPH18130' was first vegetatively propagated by terminal tip cuttings and tissue culture in Latina, Italy. 'KLEPH18130' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Black-purple flowers with a yellow border; and
2. A semi-trailing habit.

DESCRIPTION OF THE PHOTOGRAPH

This new *Petunia* plant is illustrated by the accompanying photograph of a plant grown in a plastic greenhouse in Stuttgart, Germany. The photograph was taken in April 2018 and shows the foliage and flowers of a 10-week-old plant grown indoors. The colors shown are as true as can be reasonably obtained by conventional photographic procedures.

DESCRIPTION OF THE NEW VARIETY

The following detailed descriptions set forth the distinctive characteristics of 'KLEPH18130'. The data which define these characteristics were collected from asexual reproductions carried out in Latina, Italy. Data was collected on plants grown for six weeks in a glass greenhouse followed by four weeks of outdoor cultivation in Latina, Italy in May 2019. Color references are to The R.H.S. Colour Chart of The Royal Horticultural Society of London (R.H.S.), 5$^{th}$ edition (2007).

Classification:
- *Family.*—Solanaceae.
- *Botanical.—Petunia hybrida.*
- *Common.—Petunia.*
- *Designation.*—'KLEPH18130'.

Parentage:
- *Female parent.*—The proprietary female *Petunia* variety 'PH-2014-0317' (unpatented).
- *Male parent.*—The proprietary male *Petunia* variety 'PH-2014-0319' (unpatented).

Plant:
- *Vigor.*—Medium-compact.
- *Habit.*—Semi-trailing.
- *Height (from top of soil).*—12.0 cm.
- *Width (horizontal plant diameter).*—30.0 cm.
- *Propagation.*—Terminal tip cuttings.
- *Time to produce a finished flowering plant.*—About 14 weeks in the winter under short. day conditions, and 7 weeks in the spring.
- *Time to initiate and develop roots.*—2 to 3 weeks.
- *Root description.*—Moderate density, moderate branching, white roots.

Stems:

*Average number* (*basal*).—10.

*Length of basal branches* (*from the base of the stem to the tip*).—18.0 cm.

*Internode length*.—About 4.0 cm at mid length.

*Diameter of branches* (*from midpoint*).—0.25 cm.

*Stem color*.—RHS 144 A.

*Anthocyanin*.—Absent.

*Texture*.—Pubescent.

Leaves:

*Arrangement*.—Alternate along the stem, opposite under the inflorescence.

*Length*.—About 5.0 cm.

*Width*.—About 2.4 cm.

*Shape*.—From elliptic to slightly ovate.

*Apex*.—Acute.

*Base*.—Attenuate.

*Margin*.—Entire.

*Immature leaf color*.—Upper surface: RHS 137C. Lower surface: RHS 146B.

*Mature leaf color*.—Upper surface: RHS 146A. Lower surface: RHS 146C.

*Texture* (*both upper and lower surfaces*).—Pubescent.

*Venation pattern*.—Arcuate.

*Venation color*.—Upper surface: RHS 144A. Lower surface: RHS 144B.

*Petioles*.—Length: 0.7 cm. Diameter: 0.3 cm. Color: Between RHS N79A and RHS79A, RHS 160C at the border. Texture: Pubescent.

Flower buds:

*Shape*.—Irregular oblong.

*Length*.—About 4.0 cm.

*Diameter*.—0.6 cm.

*Color at tight bud*.—RHS N77A with RHS 1A margins.

*Texture*.—Pubescent.

Inflorescence:

*Blooming habit* (*flowering season*).—Continuous flowering during spring and summer time.

*Inflorescence type*.—Sympodial, with monochasial growth.

*Number of flowers per node*.—1.

*Lastingness of individual blooms on the plant*.—About 7 days.

*Fragrance*.—Not detected.

*Flowers*.—Arrangement: Composed of 5 petals fused at the base. Diameter (flower face): 5.0 cm. Depth (total length of flower): 4.8 cm. Throat/Funnel: Length: 2.7 cm. Diameter (at opening): 1.0 cm. Texture: Inner surface: Smooth. Outer surface: Pubescent. Color: Inner surface: RHS 203A. Outer surface: RHS 79A. Petals: Color of petals, mature flower (fully opened): Upper surface: Tone of the main color can vary during the season from RHS N92A to RHS N 81A with an RHS 1D border, thickness of the border can also vary. Lower surface: RHS N92A to RHS 79D with an RHS 1C border. Apex: Slightly mucronate. Base: Fused. Shape: Salverform. Margin: Entire. Strength of waviness: Weak. Degree of lobation: Average. Calyx arrangement: Whorl of 5 sepals, fused at the base. Sepals: Color: Upper surface: RHS 137B. Lower surface: RHS 137D. Length: 1.7 cm to 2.0 cm. Width: 0.4 cm. Shape: Oblanceolate. Apex: Broadly acute. Base: Attenuate. Margin: Entire. Texture (both upper and lower surfaces): Pubescent.

*Pedicels*.—Color: RHS 144C. Length: 1.7 cm to 2.5 cm. Diameter: 0.15 cm. Texture: Pubescent.

Reproductive organs:

*Stamens*.—Quantity: 5. Shape: Needle with elliptic head. Filament: Length: 1.0 cm to 1.9 cm. Diameter: 0.02 cm. Color: RHS N79A. Anther: Shape: Elliptic. Color: RHS 145C. Length: 0.25 cm. Diameter: 0.2 cm. Pollen: Color: RHS 4D. Amount: Abundant.

*Pistils*.—Quantity per flower: 1. Length: 2.5 cm. Stigma color: RHS 143B. Style color: RHS 146C (shades of RHS N177C at the midpoint, RHS 138B at the base).

Fruit and seed set: No fruit and seed set observed to date.

Disease and pest/insect resistance: No disease and pest/insect resistance observed.

COMPARISON WITH PARENTAL LINES AND KNOWN VARIETY

'KLEPH18130' is a distinct variety of *Petunia* and is distinguished from its parents as described in Table 1.

TABLE 1

Comparison with Parental Lines

| Characteristic | Variety 'KLEPH18130' | Female parent 'PH-2014-0317' | Male Parent 'PH-2014-0319' |
|---|---|---|---|
| Flower color | Black purple with yellow border | Magenta with white zones | Purple with black eye and white zones |

'KLEPH18130' is a distinct variety of *Petunia* and differences between 'KLEPH18130' and the commercial variety *Petunia* Rim Magenta, patent status unknown, are described in Table 2.

TABLE 2

Comparison with Similar Variety

| Characteristic | Variety 'KLEPH18130' | Commercial line 'Petunia Rim Magenta' |
|---|---|---|
| Flower color | Black purple with yellow border | Purple with white yellowish border |

We claim:

1. A new and distinct variety of *petunia* plant named 'KLEPH18130' as illustrated and described herein.

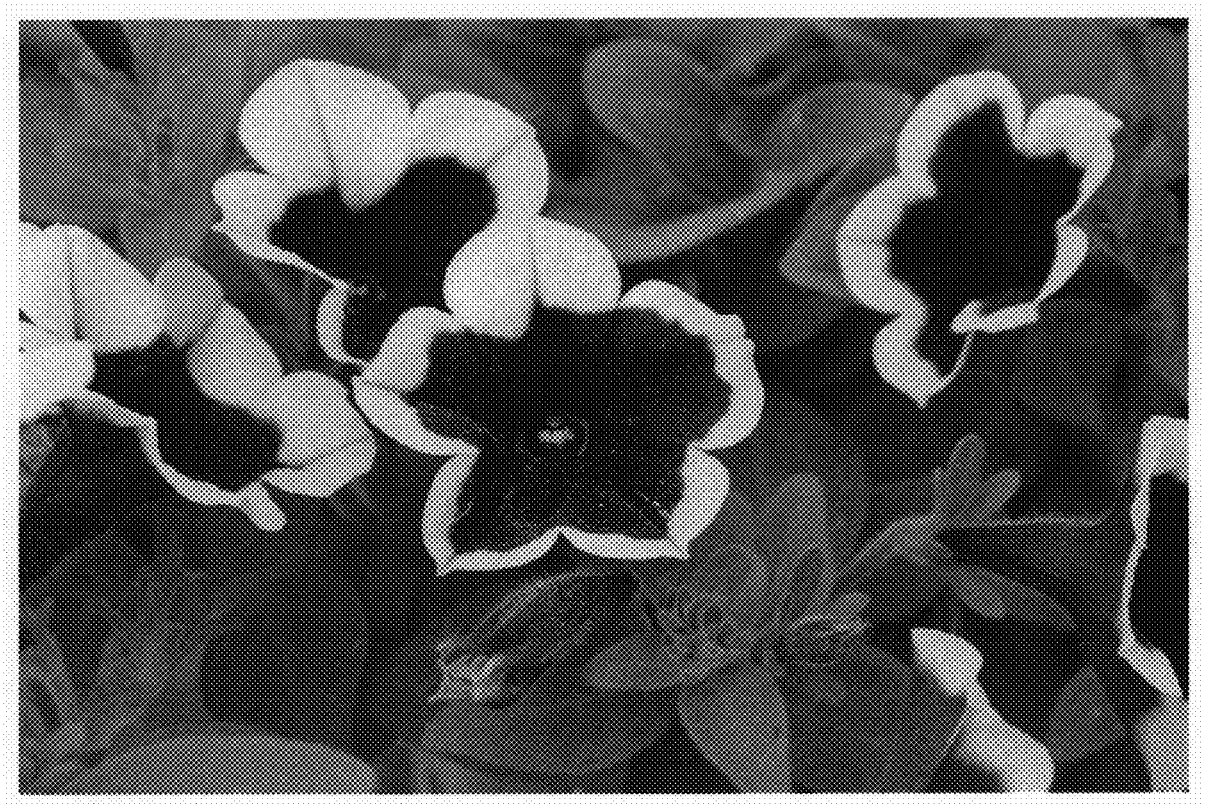

* * * * *